United States Patent [19]

Weber et al.

[11] Patent Number: 5,072,037
[45] Date of Patent: Dec. 10, 1991

[54] PROCESS FOR THE PREPARATION OF 2-(4-CHLOROPHENYL)-3-METHYL-BUTYRIC ACID

[75] Inventors: Jürgen Weber, Oberhausen; Peter Lappe, Dinslaken; Helmut Springer, Oberhausen, all of Fed. Rep. of Germany

[73] Assignee: Hoechst Aktiengesellschaft, Fed. Rep. of Germany

[21] Appl. No.: 632,471

[22] Filed: Dec. 21, 1990

[30] Foreign Application Priority Data

Dec. 23, 1989 [DE] Fed. Rep. of Germany ....... 3942790

[51] Int. Cl.$^5$ .............................................. C07C 51/16
[52] U.S. Cl. .................................. 562/419; 562/418; 568/429; 568/812; 570/182
[58] Field of Search ................ 562/418, 419; 568/429, 568/812; 570/182

[56] References Cited

U.S. PATENT DOCUMENTS 4,694,100  9/1987  Shimizu ............................. 562/419
4,814,494  3/1989  Shimizu ............................. 562/419

OTHER PUBLICATIONS

Chemical Abstracts, Band 105, No. 78,666c, Sep. 1986.
Chemical Abstracts, Band 105, No. 78,660w, Sep. 1986.
Chemical Abstracts, Band 82, No. 170,399x; Jun. 1975.

*Primary Examiner*—Michael L. Shippen
*Attorney, Agent, or Firm*—Jordan B. Bierman

[57] ABSTRACT

A process for the preparation of 2-(4-chlorophenyl)-3-methylbutyric acid from 4-chlorobenzaldehyde by conversion of the benzaldehyde to 3-(4-chlorophenyl)-2-methylpropenal, 3-(4-chlorophenyl)-2-methylpropanol, 1-(4-chlorophenyl)-2-methylpropene-1, and 2-(4-chlorophenyl)-2-methylbutyraldehyde, and finally to the desired corresponding butyric acid.

21 Claims, No Drawings

PROCESS FOR THE PREPARATION OF 2-(4-CHLOROPHENYL)-3-METHYLBUTYRIC ACID

This Application claims the priority of German Application P 39 42 790, filed Dec. 23, 1989.

The invention relates to a novel process for the preparation of 2-(4-chlorophenyl)-3-methylbutyric acid.

BACKGROUND OF THE INVENTION

The compound mentioned belongs to the class of substituted phenylacetic acid derivatives which are useful intermediate products for insecticides, pharmaceuticals, and agricultural chemicals. In accordance with their use, emphasis is placed on a high purity of these compounds, because impurities severaly impair the quality and activity of the end products.

Various processes are known for the preparation of substituted phenylacetic acid derivatives, and in particular 2-(4-chlorophenyl)-3-methylbutyric acid.

Thus, according to British Patent 1,528,043, 4-halogenobenzyl halides 4-X-$C_6H_4$-$CH_2$X (wherein X is individually Cl, Br, or I) are reacted with approximately an equimolar amount of an alkali metal cyanide and a quaternary ammonium compound. A benzylnitrile derivative is formed, which is reacted with a molar excess of a secondary alkyl chloride in the presence of an alkali metal hydroxide; the product can then be hydrolyzed to the carboxylic acid.

According to C.A. 105 (1986), 78660w, 4-chlorophenyl isopropyl ketone is methylated with a sulfonium salt, the epoxide formed is isomerized with a Lewis or Bronsted acid, and the resulting aldehyde is oxidized to 2-(4-chlorophenyl)-3-methylbutyric acid.

Finally, the preparation of 2-(4-chlorophenyl)-3-methylbutyric acid from 4-chlorophenyl 2-methylpropyl ketone is described in the published Japanese Patent Application 79/84,543. The ketone is converted into an enamine by reaction with a secondary amine and a dehydrating agent.

Reaction of the enamine with the azide of a phosphoric acid ester gives an amidine, hydrolysis of which leads to 2-(4-chlorophenyl)-3-methylbutyric acid.

However, the known processes do not meet all the requirements imposed on a modern chemical process used commercially. In addition to the above-mentioned high purity of the reaction product, it is expected that the starting substances are readily available, no by-products which pollute the environment are formed, and at least good yields are achieved.

BRIEF DESCRIPTION OF THE INVENTION

It is, therefore, the object of this invention to provide a process which meets these requirements, is economical, and can be carried out industrially without problems. According to the invention, this object is achieved by a process which comprises reacting 4-chlorobenzaldehyde with propionaldehyde to give 4-(4-chlorophenyl)-2-methylprepanal, hydrogenating the propenal derivative to form 3-(4-chlorophenyl)-2-methylpropanol, dehydrating the alcohol to form 1-(4-chlorophenyl)-2-methylpropene-1, hydroformylating this substituted propylene and oxidizing the 2-(4-chlorophenyl)-3-methylbutyraldehyde formed to give 2-(4-chlorophenyl)-3-methylbutyric acid.

This novel procedure is distinguished by the fact that it employs inexpensive starting materials which are available in industrial amounts, contains reaction steps which are easy to perform industrially, and gives the desired product in the pure form and in good yields. Moreover, no environment-polluting waste substances are formed.

DETAILED DESCRIPTION OF THE INVENTION

The aldol condensation of the 4-chlorobenzaldehyde with propionaldehyde, which proceeds by splitting off water, is carried out under the catalytic influence of alkali metal hydroxides, alkali metal carbonates or amines, preferably alkali metal hydroxides, such as NaOH.

The two aldehydes are employed in a molar ratio of 1:1 to 1:2, preferably 1:1.1 to 1:1.3. The amount of catalyst is 0.1 to 0.5 mol per mole of 4-chlorobenzaldehyde. The alkali metal hydroxide and alkali metal carbonate are usually used as aqueous solutions. It is advisable to employ solutions which contain the alkali metal compounds in amounts of 10 to 100 g, preferably 25 to 75 grams per liter of solution. The reaction usually goes to completion at temperatures of 80° to 120°, preferably 95° to 105° C. The yield is approximately 90% of theoretical, based on the 4-chlorobenzaldehyde. The starting substances can be used in the commercially available purity. To isolate the 3-(4-chlorophenyl)-2-methylpropenal, the organic phase is separated off from the aqueous phase. For further processing it is sufficient to wash the product once with water.

In the next reaction step, the unsaturated aldehyde is hydrogenated to the corresponding saturated alcohol, 3-(4-chlorophenyl)-2-methylpropanol. The reaction with hydrogen is carried out in the liquid phase in the presence of a catalyst containing nickel. It has proved appropriate to employ those catalysts which contain 20 to 60, and in particular 40 to 55% by weight of nickel (based on the total catalyst), and in addition supports and, if appropriate, activators. Aluminum oxide or kieselguhr is suitable as the support material. A catalyst containing 50 to 55% by weight of nickel and in addition kieselguhr as the support is preferred. Depending on the composition of the catalyst, the hydrogenation temperature is in general in the range from 80° to 120° C. 3-(4-chlorophenyl)-2-methylpropanol having a selectivity of 90% or more is obtained at 95 to 97% conversion of the unsaturated aldehyde employed. After the hydrogenation catalyst has been removed, the alcohol can be subjected to the dehydration reaction directly, i.e. again without prior purification.

In some cases, however, it is advantageous for the alcohol first to be prepurified by coarse distillation, so that it is present in a purity of more than 98%. The dehydration of the 3-(4-chlorophenyl)-2-methylpropanol to 1-(4-chlorophenyl)-2-methylpropene-1 and -propene-2 is carried out in the vapor phase at temperatures between 280° and 340° C. in the presence of a catalyst containing predominantly aluminum oxide. Catalysts which also contain silicon dioxide in addition to aluminum oxide are particularly successfully employed. Surprisingly, the dehydration of the alcohol in the presence of such catalysts proceeds without formation of products having an isomerized carbon structure; this occurring to a considerable degree when other catalysts are used. A conversion of >95% is achieved at temperatures of 310° to 330° C. and a space velocity of 0.1 to 0.5 $m^3/h·m^3$. To increase the 1-(4-chlorophenyl)-2-methylpropene-1 content, the product is isomerized in the presence of an acid catalyst, preferably sulfuric acid, and then worked up by distillation on a column having 20 to 60 theoretical plates. 1-(4-chlorophenyl)-2-methylpropene-1 is obtained after distillation in a yield of more than 65%, based on the alcohol employed.

The propene derivative obtained by dehydration of the alcohol can be hydroformylated directly without prior working up or purification. Preferably, however, an olefin purified by fractional distillation should be employed in the hydroformylation reaction. The reaction is carried out, as is customary, in the presence of carbonyl-forming metals of group VIII of the Periodic Table (IUPAC Version). The use of rhodium as the catalyst, which is contained in the reaction mixture in the form of a rhodium carbonyl complex, has proved particularly appropriate. In practice, the substituted propene and a rhodium salt, for example rhodium chloride or rhodium 2-ethylhexanoate, are initially introduced into a pressure vessel. The Rh concentration is 10 to 1000 ppm, based on the olefin employed. Carbon monoxide and hydrogen are advantageously fed to the reactor in a ratio of 1:1, and the reaction proceeds at 100° to 160° C. under a pressure of 15 to 30 MPa. The carbon monoxide/hydrogen mixture is fed to the reactor at a rate such that the chosen reaction pressure is maintained. The use of rhodium catalysts ensures that the olefin is virtually completely converted into a mixture of 2-(4-chlorophenyl)-3-methylbutanal and 3-(4-chlorophenyl)-2,2-dimethylpropanal. No alcohols are formed. Moreover, no other by-products are formed by isomerization of the starting olefin. The hydroformylation product is worked up in a known manner by removal of the catalyst and distillation. This result is a mixture of 96 to 97% by weight of 2-(4-chlorophenyl)-3-methylbutanal and 3 to 4% by weight of 3-(4-chlorophenyl)-2,2-dimethylpropanal which contains impurities only to a minor extent.

This aldehyde mixture is reacted with oxidizing agents, such as potassium permanganate, hydrogen peroxide, sodium hypochlorite and others to give a mixture of the corresponding acids.

The reactions are carried out, for example, at temperatures of 10° to 30° C. if potassium permanganate is used as the oxidizing agent and dilute sulfuric acid is present. The oxidizing agent is employed in an amount of 1 to 1.5 mol per mole of aldehyde. A similar procedure is followed if the oxidation is carried out with sodium hypochlorite or hydrogen peroxide.

When the reaction is complete, a suitable solvent, aromatic hydrocarbons, such as toluene or xylene, being preferred, is added to the reaction mixture. The organic phase is separated and removed from the solvent in vacuo in rotary evaporator. The residue is recrystallized for purification. Cyclohexane, for example, has proved suitable for this.

The following examples are intended to illustrate the invention but are not considered to be limitative.

EXAMPLE 1

Preparation of 3-(4-chlorophenyl)-2-methylpropenal 500 g (3.56 mol) of 4-chlorobenzaldehyde and 569.6 g (0.712 mol) of 5% by weight sodium hydroxide solution are initially introduced into a 2 liter three-necked flask fitted with a stirrer, a reflux condenser, an internal thermometer, and a dropping funnel, in the presence of a nitrogen atmosphere. The mixture is heated to 100° C. and 227.8 g (3.93 mol) of propionaldehyde are added dropwise in the course of one hour, and the mixture is allowed to after-react under reflux at about 103° C. for a further hour. 356 g of toluene are then added, the contents of the flask are cooled to about 50° C. An organic phase (1031.3 g) and an aqueous phase (622.1 g) are obtained, and the phases are separated. The organic phase is washed once with 178 g of water. After renewed separation of the phases, a wash water phase (199.4 g) and the useful product phase (1009.9 g), which is analyzed by gas chromatography, are obtained.

| GLC analysis: | |
|---|---|
| Toluene | 41.05% by weight |
| 2-Methylpentenal | 1.84% by weight |
| 4-Chlorobenzaldehyde | 3.16% by weight |
| 3-(4-chlorophenyl)-2-methylpropenal | 52.68% by weight |
| Others | 1.27% by weight |

This shows a 3-(4-chlorophenyl)-2-methylpropenal yield of 90.8% of theoretical, based on the 4-chlorobenzaldehyde.

EXAMPLE 2 TO 8

Further Examples of the Preparation of 3-(4-chlorophenyl)-2-methylpropanal

Reactions for the preparation of 3-(4-chlorophenyl)-2-methylpropenal are carried out in accordance with Example 1 under the conditions set forth in Table 1.

TABLE 1

| Example | Feed ratio (mol) 4-Chlorobenzaldehyde | Propionaldehyde | NaOH | NaOH concentration (%) | Temperature (°C.) | Solvent | GLC analysis (in % by weight) 1 | 2 | 3 | 4 | 5 | Yield (% of theory) |
|---|---|---|---|---|---|---|---|---|---|---|---|---|
| 2 | 1 | 1.15 | 0.20 | 5.0 | 95 | Toluene | 40.44 | 2.61 | 2.86 | 50.77 | 3.32 | 87.7 |
| 3 | 1 | 1.20 | 0.20 | 5.0 | 100 | Toluene | 40.87 | 3.26 | 2.11 | 51.12 | 2.64 | 88.7 |
| 4 | 1 | 1.25 | 0.20 | 5.0 | 100 | Toluene | 40.13 | 3.85 | 2.08 | 51.41 | 2.53 | 94.8 |
| 5 | 1 | 1.20 | 0.25 | 5.0 | 100 | Toluene | 40.79 | 3.18 | 1.73 | 51.63 | 2.67 | 88.8 |
| 6 | 1 | 1.20 | 0.20 | 7.5 | 103 | Toluene | 41.16 | 3.26 | 2.03 | 51.00 | 2.55 | 93.1 |
| 7 | 1 | 1.20 | 0.15 | 7.5 | 103 | Toluene | 41.12 | 2.85 | 1.70 | 51.84 | 2.49 | 90.4 |
| 8 | 1 | 1.20 | 0.20 | 5.0 | 102 | Cyclohexane | 39.87 | 2.70 | 1.40 | 54.34 | 1.69 | 92.1 |

1: Solvent
2: 2-Methylpentenal
3: 4-Chlorobenzaldehyde
4: 3-(4-Chlorophenyl)-2-methylpropenal
5: Others

EXAMPLE 9

Preparation of 3-(4-chlorophenyl)-2-methylpropanol

For hydrogenation of 3-(4-chlorophenyl)-2-methylpropenal, an aldolization product (similar to those of Examples 1-8) of the following composition is used:

| | |
|---|---|
| Toluene | 41.08% by weight |
| 2-Methylpentenal | 2.56% by weight |
| 4-Chlorobenzaldehyde | 3.32% by weight |
| 3-(4-Chlorophenyl)-2-methylpropenal | 51.01% by weight |
| Others | 2.03% by weight |

500 g of the above composition and 25 g of nickel catalyst (52% by weight of Ni on a support) are hydrogenated at 90° C. under a hydrogen pressure of 10 MPa in a 1 liter autoclave, the reaction time being about 6 hours. After the contents of the reactor have cooled, the catalyst is separated off and the organic phase (502 g) is analyzed by gas chromatography.

| GLC analysis: | |
|---|---|
| Toluene | 47.82% by weight |
| 2-Methylpentenol | 1.26% by weight |
| 4-Chlorobenzyl alcohol | 1.85% by weight |
| 3-(4-Chlorophenyl)-2-methylpropenal | 44.07% by weight |
| Others | 5.00% by weight |

The yield, determined by gas chromatography, is 86.8% of theoretical.

EXAMPLE 10

Preparation of 1-(4-chlorophenyl)-2-methylpropene-1

The dehydration of the hydrogenation product of Example 9 is carried out in 300 ml of a gamma-Al$_2$O$_3$ catalyst in a reaction tube 120 cm long. A 30 cm high stack of Raschig rings is located above the catalyst (about 80 cm) and functions as an evaporator zone. When the reaction temperature of 320° C. is reached in the uniformly heated furnace, 5000 g of the hydrogenated product of Example 9 are introduced into the tube from the top at a space velocity of 0.2 V/Vh by means of a metering pump. During this operation, the product evaporates in the Raschig ring zone and meets the catalyst in gaseous form. At the lower outlet of the reaction tube is an intensive condenser in which the reaction mixture is condensed and drops into the final round-bottomed flask. After separation of the phases, the organic product is analyzed by gas chromatography.

| GLC analysis: | |
|---|---|
| Toluene | 44.49% by weight |
| 1-(4-Chlorophenyl)-2-methylpropene-2 | 32.86% by weight |
| 1-(4-Chlorophenyl)-2-methylpropene-1 | 12.42% by weight |
| 3-(4-Chlorophenyl)-2-methylpropanol | 2.30% by weight |
| Others | 7.92% by weight |

Distillation in a column having 24 theoretical plates at a reflux ratio of 3:1, an overhead temperature of 103° to 113° C., and a pressure of 3 kPa gives a main fraction of the following composition:

| | |
|---|---|
| 1-(4-chlorophenyl)-2-methylpropene-2 | 71.92% by weight |
| 1-(4-chlorophenyl)-2-methylpropene-1 | 25.69% by weight |
| Others | 2.39% by weight |

1000 g of the above olefin mixture are isomerized in a 4 liter round-bottomed flask by addition of 1000 g of 50% by weight sulfuric acid at 120° C. for 9 hours. According to analysis by gas chromatography, the reaction product contains 18.31% by weight of 1-(4-chlorophenyl)-2-methylpropene-2 and 76.94% by weight of 1-(4-chlorophenyl)-2-methylpropene-1, as well as 4.75% by weight of other by-products.

Working up by distillation in a column having 24 theoretical plates yields 1392 g of a main fraction which contains 94.33% by weight of 1-(4-chlorophenyl)-2-methylpropene-1, 2.51% by weight of 1-(4-chlorophenyl)-2-methylpropene-2, and 3.16% by weight of other secondary components. The yield is 66.0% of theoretical, based on the 3-(4-chlorophenyl)-2-methylpropanol employed.

EXAMPLE 11

Preparation of 2-(4-chlorophenyl)-3-methylbutanal

The substituted propene-1 of Example 10 is mixed with cyclohexane in a weight ratio of 1:1; 1100 g of the mixture are hydroformylated in a 2 liter autoclave which is equipped with an up and down stirrer. The reaction takes place at 120° C. under a pressure of 27 MPa in the presence of 100 ppm of rhodium (based on the substituted propene-1) as the catalyst. After a reaction of about 14 hours, the contents of the autoclave (1187 g) are cooled and analyzed by gas chromatography.

| GLC analysis: | |
|---|---|
| Cyclohexane | 52.67% by weight |
| 1-(4-Chlorophenyl)-2-methylpropene-1 | 2.05% by weight |
| 2-(4-Chlorophenyl)-3-methylbutanal | 32.42% by weight |
| 3-(4-Chlorophenyl)-2,2-dimethylpropanal | 9.15% by weight |
| Others | 3.71% by weight |

The hydroformylation product is distilled in two stages in a thin film evaporator. The cyclohexane is first separated at a jacket temperature of 140° C. under normal pressure, and the residue (925.7 g corresponding to 78.0% of the feed) is then distilled at a jacket temperature of 180° C. under a pressure of 2 kPa. The distillate (648.0 g corresponding to 54.6% of the feed) contains 64.4% by weight of 2-(4-chlorophenyl)-3-methylbutanal, 19.20% by weight of 3-(4-chlorophenyl)-2,2-dimethylpropanal, 4.45% by weight of cyclohexane, and 11.95% by weight of other secondary components.

Therefore, fractional distillation in a column having 24 theoretical plates and a reflux ratio of 3:1, yields a main fraction (401.7 g corresponding to 33.8% of the feed) which boils at 115° to 117° C. under 7 mbar pressure and contains 96.42% by weight of 2-(4-chlorophenyl)-3-methylbutanal. The yield is, therefore, 69.6% of theoretical, based on the 1-(4-chlorophenyl)-2-methylpropene-1 employed.

EXAMPLE 12

Preparation of 2-(4-chlorophenyl)-3-methylbutyric acid 100 g (0.49 mol) of 96.42% by weight 2-(4-chlorophenyl)-3-methylbutanal (the product of Example 11) and 558.4 g of 19.4% by weight sulfuric acid are initially introduced into a 1 liter three-necked flask fitted with a stirrer, a reflux condenser, a dropping funnel, and an internal thermometer. Thereto, 79.05 g (0.5 mol) of $KMnO_4$ are added at 20° to 25° C. in the course of 2 hours. After an after-reaction of one hour at 20° to 25° C., 600 g of toluene are introduced. The solid is filtered off and the organic phase is separated from the aqueous phase. The organic phase is freed from the toluene on a rotary evaporator and the residue is recrystallized from cyclohexane.

The yield is 86.4 g corresponding to 82.8% of theoretical (based on the aldehyde employed), and the product has a melding point of 89° to 91° C.

What we claim is:

1. A process for the preparation of 2-(4-chlorophenyl)-3-methylbutyric acid comprising
   aldol condensation of 4-chlorobenzaldehyde and propionaldehyde to produce 3-(4-chlorophenyl)-2-methylpropenal as a propenal derivative,
   hydrogenation of said propenal derivative to form 3-(4-chlorophenyl)-2-methylpropanol,
   dehydration of said methylpropanol to provide 1-(4-chlorophenyl)-2-methylpropene-1,
   hydroformylation of said methylpropene-1 to yield 2-(4-chlorophenyl)-3-methylbutyraldehyde; and
   oxidation of said butyraldehyde to said butyric acid contained in an oxidation product.

2. The process of claim 1 wherein said benzaldehyde and said propionaldehyde are present in a molar ratio of 1 to 1–2.

3. The process of claim 2 wherein said molar ratio is 1 to 1.1–1.3.

4. The process of claim 1 wherein said aldol condensation is in the presence of sodium hydroxide.

5. The process of claim 4 wherein said sodium hydroxide is present in an amount of 0.1 to 0.5 mols per mol of said benzaldehyde.

6. The process of claim 1 wherein said hydrogenation is carried out in liquid phase.

7. The process of claim 6 wherein said hydrogenation is in the presence of a catalyst containing 20% to 60% by weight of nickel based on the total of said catalyst.

8. The process of claim 7 wherein said catalyst contains 40% to 55% by weight of nickel based on the total of said catalyst.

9. The process of claim 8 wherein said catalyst contains 50% to 55% by weight of nickel based on the total of said catalyst, kieselguhr being present as a support.

10. The process of claim 1 wherein said dehydration is in the presence of dehydration catalyst to yield a dehydration mixture comprising said 1-(4-chlorophenyl)-2-methylpropene-1 and 1-(4-chlorophenyl)-2-methylpropene-2.

11. The process of claim 10 wherein said dehydration catalyst is predominantly $Al_2O_3$.

12. The process of claim 11 wherein said dehydration catalyst contains $SiO_2$.

13. The process of claim 11 wherein said dehydration takes place at 280° to 340° C.

14. The process of claim 10 wherein said dehydration is carried out at a dehydration temperature of 310° to 330° C. and a space velocity of 0.1 to 0.5 $m^3/h \cdot m^3$.

15. The process of claim 10 wherein said dehydration mixture is isomerized in the presence of acid catalyst.

16. The process of claim 15 wherein said acid catalyst is sulfuric acid.

17. The process of claim 1 wherein said hydroformylation takes place at elevated temperature and pressure in the presence of a rhodium catalyst.

18. The process of claim 1 wherein said oxidation is in the presence of an oxidizing agent selected from the group consisting of potassium permanganate, hydrogen peroxide, and sodium hypochlorite.

19. The process of claim 18 wherein said oxidation takes place at 10° to 30° C.

20. The process of claim 1 wherein said oxidation product is subjected to recrystallization.

21. The process of claim 20 wherein said recrystallization is from cyclohexane.

* * * * *